United States Patent [19]
Bordignon et al.

[11] Patent Number: 6,074,836
[45] Date of Patent: *Jun. 13, 2000

[54] METHOD OF MARKING EUKARYOTIC CELLS

[75] Inventors: Claudio Bordignon; Fulvio Mavilio, both of Milan, Italy

[73] Assignee: Boehringer Mannheim GmbH, Mannheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/602,791

[22] PCT Filed: Aug. 11, 1994

[86] PCT No.: PCT/EP94/02687

§ 371 Date: Apr. 4, 1996

§ 102(e) Date: Apr. 4, 1996

[87] PCT Pub. No.: WO95/06723

PCT Pub. Date: Mar. 9, 1995

[30] Foreign Application Priority Data

Sep. 1, 1993 [IT] Italy ................................ RM93A0587

[51] Int. Cl.$^7$ ............................. C12N 5/00; G01N 33/53; A01N 63/00
[52] U.S. Cl. ........................ 435/7.24; 435/7.21; 435/366; 435/372.3; 424/93.21
[58] Field of Search .......................... 435/172.3, 2, 7.21, 435/7.24, 372.3, 366; 424/93.1, 93.2, 93.21

[56] References Cited

U.S. PATENT DOCUMENTS

| | | | |
|---|---|---|---|
| 5,055,459 | 10/1991 | Andersson et al. | 514/114 |
| 5,470,730 | 11/1995 | Greenberg et al. | 435/172.3 |

FOREIGN PATENT DOCUMENTS

| | | |
|---|---|---|
| 0 455 460 A2 | 11/1991 | European Pat. Off. . |
| WO 91/16069 | 10/1991 | WIPO . |
| WO 92/01810 | 2/1992 | WIPO . |
| WO 92/05262 | 4/1992 | WIPO . |
| WO 92/08796 | 5/1992 | WIPO . |
| WO 92/09631 | 6/1992 | WIPO . |
| WO 92/19749 | 11/1992 | WIPO . |
| WO 93/04167 | 3/1993 | WIPO . |

OTHER PUBLICATIONS

Rowley, S., et al., Bone Marrow and Stem Cell Processing: A Manual of Current Techniques, F.A. Davies Co., Philadelphia: 218–291 (1992).

Bonini, C., et al., "Transfer of the HSV–TK gene into donor peripheral blood lymphocytes for in vivo immunomodulation of donor anti–tumor immunity after allo–bmt", Blood 84 (10), Suppl. 1:110a (1994).

Bordignon, C., et al., "Transfer of the HSV–tk Gene into Donor Peripheral Blood Lymphocytes for In Vivo Modulation Donor Anti–Tumor Immunity after Allogeneic Bone Marrow Transplantation", Human Gene Therapy 6:813–819 (1995).

Database WPI, Week 9308, Derwent Publications Ltd., London GB; AN 93–067423 & US–A 7 779 195 (U.S. Department of Health & Human Service), Dec. 15, 1992, NTIS publication of US–Published–Application–7779195.

Gillio, A., et al., "Retroviral Vector–mediated Gene Transfer and Expression in Nonhuman Primates Following Autologous Bone Marrow Transplantation", Annals New York Academy of Sciences 511:406–417 (1987).

Keller, G., et al., "Expression of a foreign gene in myeloid and lymphoid cells dervived from multipotent haematopoietic precursors", Nature 318:149–154 (1985).

Servida, P., "Gene transfer into peripheral blood lymphocytes for in vivo immunomodulation of donor anti–tumor immunity in a patient affected by EBV–induced lymphoma", Blood 82 (10), Suppl. 1:214a (1993).

Areman et al., Bone Marrow Transplant, vol. 18, No. 3, pp. 521–525 (1996), "Hematopoietic potential of IL–2–cultured peripheral blood stem cells from breast cancer patients".

Areman et al., Transfus. Med. Rev., vol. 5, No. 3, pp. 214–227 (1991), "Bone marrow processing for transplantation".

Areman et al., Transfusion, vol. 31, No. 8, pp. 724–730 (1991), "Automated processing of human bone marrow can result in a population of mononuclear cells capable of achieving engraftment following transplantation".

Juneja et al., Leukemia, vol. 9, No. 10, pp. 1771–1778 (1995), "Successful in vitro purging of leukemic blasts from marrow by cortivazol, a pyrazolosteroid: a preclinical study for autologous transplantation in acute lymphoblastic leukemia and non–Hodgkin's lymphoma".

Negrin et al., Blood, vol. 85, No. 11, pp. 3334–3341 (1995), "Transplantation of enriched and purged peripheral blood progenitor cells from a single apheresis product in patients with non–Hodgkin's lymphoma".

Rubin et al., J. Hemather. vol. 3, No. 2, pp. 121–127 (1994), "A combination of anti–CD15 monoclonal antibody PM–81 and 4–hydroperoxycyclophosphamide augments tumor cytotoxicity while sparing normal progenitor cells".

Soiffer et al., Bone Marrow Transplant, vol. 12, No. 3, pp. 243–251 (1993), "Monoclonal antibody–purged autologous bone marrow transplantation in adults with acute lymphoblastic leukemia at high risk of relapse".

Volger et al., J. Hemather., vol. 2, No. 1, pp. 93–102 (1993), "Autologous bone marrow transplantation with alkyl–lysophospholipid–purged marrow".

Gribben et al., Leuk. Lymphoma, vol. 11, Suppl. 2, pp. 141–148 (1993), "Bone marrow purging for autologous bone marrow transplantation".

(List continued on next page.)

Primary Examiner—Bruce R. Campell
Attorney, Agent, or Firm—Nikaido Marmelstein Murray & Oram, LLP

[57] ABSTRACT

A method of marking a eukaryotic (mammalian) cell by expressing in this cell a nucleic acid, said nucleic acid encoding a cell surface receptor, and by subsequently presenting said receptor at the cell surface, characterized by using a nucleic acid in which the region encoding the intracellular domain of the receptor has been completely or party deleted or modified in such a way that the receptor presented at the surface cannot, after binding to its binding partner, effect any signal transduction, is effective and usable in gene therapy.

25 Claims, 5 Drawing Sheets

OTHER PUBLICATIONS

Stiff et al., Blood, vol. 77, No. 2, pp. 355–362 (1991), "Anti–CD33 monoclonal antibody and etoposide/cytosine arabinoside combinations for the ex vivo purification of bone marrow in acute nonlymphocytic leukemia".

Prejers et al., Br. J. Haematol., vol. 71, No. 2, pp. 195–201 (1989), "Cytotoxic potential of anti–CD7 immunotoxin (WT1–ricin A) to purge ex vivo malignant T cells in bone marrow" immunological monitoring.

Heslop et al., Human Gene Therapy, vol. 5, No. 3, pp. 381–397 (1994), "Administration of neomycin resistance gene marked EBV specific cytotoxic T lymphocytes to recipients of mismatched–related or phenotypically similar unrelated donor marrow grafts".

Freeman et al., J. Cell. Biochem., Suppl. 16F, p. 47 (1992)"Tumor regression when a fraction of the tumor mass contains the HSV–TK gene".

Sikora, K., Trends in Biotechnology, vol. 11, No. 5, pp. 197–201 (1993), "Gene therapy for cancer".

Caruso et al., Proc. Natl. Acad. Sci. USA, vol. 89, pp. 182–186 (1992) "Selective killing of $CD4^+$ cells harboring a human immunodeficiency virus–inducible suicide gene prevents viral spread in an infected cell population".

Pardoll et al., Bone Marrow Transplantation, vol. 9, Suppl. 1, pp. 182–186 (1992), "Molecular engineering of the anti-tumor immune response".

Hérin et al., Intl. J. Cancer, vol. 39, No. 3, pp. 390–396 (1987), "Production of stable cytolytic T–cell clones directed against autologous human melanoma".

Gavioli et al.; J. Virology, vol. 673, No. 3, pp. 1572–1578 (1993), "Multiple HLA A11–restricted cytotoxic T–lymphocyte epitopes of different immunogenecities in the Epstein––Barr virus–encoded nuclear antigen 4".

Murray et al., J. Exp. Med., vol. 176, pp. 157–168 (1992), "Identification of target antigens for the human cytotoxic T cell response to Epstein–Barr virus (EBV): Implications for the immune control of EBV–positive malignancies".

Khanna et al., J. Exp. Med., vol. 176, pp. 169–176 (1992), "Localization of Epstein–Barr virus cytotoxic T cell epitopes using recombinant vaccinia: Implications for vaccine development".

Kabelitz et al., J. Mol. Cell Immunol., vol. 3, pp. 49–60 (1987), "Human cytotoxic T lymphocytes. III. Large numbers of peripheral blood T cells clonally develop into allorestricted anti–viral cytotoxic T cell populations in vitro".

Nagler–Anderson et al., Immunological Reviews, No. 103, pp. 111–125 (1988), "A comparison of the cytolytic properties of murine primary $CD8^+$ cytotoxic T lymphocytes and cloned cytotoxic T cell lines".

Carmichael et al., J. Exp. Med., vol. 177, No. 2, pp. 249–256 (1993), "Quantitative analysis of the human immunodeficiency virus type 1 (HIV–1)–specific cytotoxic T lymphocyte (CTL) response at different stages of HIV–1 infection: Differential CTL responses to HIV–1 and Epstein–Barr virus in late disease".

Bachmann et al., Current Opinion in Immunology, vol. 6, No. 2, pp. 320–326 (1994), "In–vivo versus in vitro assays for assessment of T– and B–cell function".

Cullis et al., Blood, vol. 79, pp. 1379–1380 (1992), "Donor leukocyte infusions for chronic myeloid leukemia in relapse after allogenic bone marrow transplantation".

Kolb et al., Blood, vol. 76, No. 12, pp. 2462–2465 (1990), "Donor leukocyte transfusions for treatment of recurrent chronic myelogenous leukemia in marrow transplant patients".

Rybak et al., Derwent Accession No. 93–067423, "Cytotoxic reagents that selectively kill cells e.g. T–cells—consists of mammalian protein as toxic moiety, recognition moiety binding specific cellular surface marker and liner for both moieties".

Chevalier et al., Blood, vol. 83, No. 6 (Mar. 15, 1994), pp. 1479–1485, "Expression and Functionality of the trkA Proto–Oncogene Product/NGF . . . ".

Mavillo, et al., Blood, vol. 83, No. 7 (Mar. 1, 1994), pp. 1988–1997, "Peripheral Blood Lymphocytes as Target Cells of Retroviral Vetor . . . ".

International Publication No. WO 92/09631 publised Jun. 11, 1992.

International Publication No. WO 92/19749 published Nov. 12, 1992.

International Publication No. WO 92/01810 published Feb. 6, 1992.

Radeke et al., Nature, vol. 325, Feb. 1987, "Gene transfer and molecular cloning of the rat nerve growth factor receptor".

Johnson et al., Cell, vol. 47, No. 21, 1986, pp. 545–554, "Expression and Structure of the Human NGF Receptor".

Wysocki LJ, (1978) "Panning" for lymphocytes: a method for cell selection. Proc.Natl.Acad.Sci.U.S.A. 75:2844–2848.

Hempstead BL, et al, (1990) Deletion of cytoplasmic sequences of the nerve growth factor receptor leads to loss of high affinity ligand binding. J Biol.Chem. 265:9595–9598.

Maryanski JL, et al, (1985) A simple panning method for the selection of cell surface antigen transfectants. J Immunol. Methods 79:159–165.

Reddy UR, et al, (1990) Transient expression of full–length and truncated forms of the human nerve growth factor receptor. Brain.Res.Mol.Brain.Res. 8:137–141.

Riddell et al., Science, vol. 257, pp. 238–241 (1992), "Restoration of viral immunity in immunodeficient humans by the adoptive transfer of T cell clones".

Fakhrai et al., J. Cell. Biochem., Keystone Symposia on Molecular and Cellular Biology, Suppl. 16F, p. 47, V208, Apr. 3–16, 1992, "Cytokine gene therapy of cancer using transduced fibroblasts".

Traversari et al., Immunogenetics, vol. 35, pp. 145–152 (1992), "Transfection and expression of a gene coding for a human melanoma antigen recognized by autologous cytolytic T lymphocytes".

Helg et al., Bone Marrow Transplantation, vol. 12, pp. 125–129 (1993), "Adoptive immunotherapy for recurrent CML after BMT".

Bär et al., J. Clin. Oncology, vol. 11, No. 3, pp. 513–519 (1993), "Donor leukocyte infusions for chronic myeloid leukemia relapsed after allogenic bone marrow transplantation".

Klingemann et al., Bone Marrow Transplantation, vol. 8, pp. 73–81 (1991), "Immunotherapy after bone marrow transplantation".

Van der Bruggen et al., Science, vol. 254, pp. 1643–1647 (1991), "A gene encoding an antigen recognized by cytolytic T lymphocytes on a human melanoma".

Traversari et al., J. Cell. Biochem., Suppl. 18A (Jan. 4–23, 1994), Abstract #DZ 318, p. 240, "Gene transfer into peripheral blood lymphocytes for in vivo immunomodulation of donor anti–tumor immunity in a patient affected by EBV–induced lymphoma".

Wickelgren, Science, vol. 276, p. 1646 (1997), "New lead to safer marrow transplants".

Bonini et al., Science, vol. 276, pp. 1719–1724 (1997), "HSV–TK gene transfer into donor lymphocytes for control of allogeneic graft–versus–leukemia".

SFCM (LΔNSN)

SFCMM-B (LΔNTN)

SFCMM-E

SFCMM-H

SFCMM-S

SFCMM-C

LNSN

SFCM (LΔNSN)

Schematic Flow Diagram for the Gene Marking Protocol

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 1600 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: misc_feature
        (B) LOCATION: one-of(943)
        (D) OTHER INFORMATION: /function= "PvuII cleavage site"

(ix) FEATURE:
        (A) NAME/KEY: misc_feature
        (B) LOCATION: one-of(1512)
        (D) OTHER INFORMATION: /function= "SstI cleavage site"

(xi) SEQUENCE DESCRIPTION: SEQ ID NO: 1:

```
GCCGCGGCCA GCTCCGGCGG GCAGGGGGGG CGCTGGAGCG CAGCGCAGCG CAGCCCCATC      60

AGTCCGCAAA GCGGACCGAG CTGGAAGTCG AGCGCTGCCG CGGGAGGCGG GCGATGGGGG     120

CAGGTGCCAC CGGCCGCGCC ATGGACGGGC CGCGCCTGCT GCTGTTGCTG CTTCTGGGGG     180

TGTCCCTTGG AGGTGCCAAG GAGGCATGCC CCACAGGCCT GTACACACAC AGCGGTGAGT     240

GCTGCAAAGC CTGCAACCTG GGCGAGGGTG TGGCCCAGCC TTGTGGAGCC AACCAGACCG     300

TGTGTGAGCC CTGCCTGGAC AGCGTGACGT TCTCCGACGT GGTGAGCGCG ACCGAGCCGT     360
```

```
                                            -continued

GCAAGCCGTG CACCGAGTGC GTGGGGCTCC AGAGCATGTC GGCGCCGTGC GTGGAGGCCG      420

ACGACGCCGT GTGCCGCTGC GCCTACGGCT ACTACCAGGA TGAGACGACT GGGCGCTGCG      480

AGGCGTGCCG CGTGTGCGAG GCGGGCTCGG GCCTCGTGTT CTCCTGCCAG GACAAGCAGA      540

ACACCGTGTG CGAGGAGTGC CCCGACGGCA CGTATTCCGA CGAGGCCAAC CACGTGGACC      600

CGTGCCTGCC CTGCACCGTG TGCGAGGACA CCGAGCGCCA GCTCCGCGAG TGCACACGCT      660

GGGCCGACGC CGAGTGCGAG GAGATCCCTG GCCGTTGGAT TACACGGTCC ACACCCCAG       720

AGGGCTCGGA CAGCACAGCC CCCAGCACCC AGGAGCCTGA GGCACCTCCA GAACAAGACC      780

TCATAGCCAG CACGGTGGCA GGTGTGGTGA CCACAGTGAT GGGCAGCTCC CAGCCCGTGG      840

TGACCCGAGG CACCACCGAC AACCTCATCC CTGTCTATTG CTCCATCCTG GCTGCTGTGG      900

TTGTGGGCCT TGTGGCCTAC ATAGCCTTCA AGAGGTGGAA CAGCTGCAAG CAGAACAAGC      960

AAGGAGCCAA CAGCCGGCCA GTGAACCAGA CGCCCCCACC AGAGGGAGAA AAACTCCACA     1020

GCGACAGTGG CATCTCCGTG GACAGCCAGA GCCTGCATGA CCAGCAGCCC CACACGCAGA     1080

CAGCCTCGGG CCAGGCCCTC AAGGGTGACG GAGGCCTCTA CAGCAGCCTG CCCCCAGCCA     1140

AGCGGGAGGA GGTGGAGAAG CTTCTCAACG GCTCTGCGGG GGACACCTGG CGGCACCTGG     1200

CGGGCGAGCT GGGCTACCAG CCCGAGCACA TAGACTCCTT TACCCATGAG GCCTGCCCCG     1260

TTCGCGCCCT GCTTGCAAGC TGGGCCACCC AGGACAGCGC CACACTGGAC GCCCTCCTGG     1320

CCGCCCTGCG CCGCATCCAG CGAGCCGACC TCGTGGAGAG TCTGTGCAGT GAGTCCACTG     1380

CCACATCCCC GGTGTGAGCC CAACCGGGGA GCCCCCGCCC CGCCCCACAT TCCGACAACC     1440

GATGCTCCAG CCAACCCCTG TGGAGCCCGC ACCCCCACCC TTTGGGGGGG GCCCGCCTGG     1500

CAGAACTGAG CTCCTCTGGG CAGGACCTCA GAGTCCAGGC CCCAAAACCA CAGCCCTGTC     1560

AGTGCAGCCC GTGTGGCCCC TTCACTTCTG ACCACACTTC                          1600

(2) INFORMATION FOR SEQ ID NO: 2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

TGCTGACCCC ACTGTCGACC TCCTTCCCAT T                                    31
```

METHOD OF MARKING EUKARYOTIC CELLS

The invention is related to a method of marking eukaryotic (mammalian) cells by the use of a cell surface receptor with a modified intracellular domain as a selectable marker.

The identification of cells into which a DNA sequence has been successfully introduced is an essential step in recombinant DNA technology. As the DNA sequence to be introduced will not necessarily lead to a phenotype which may be selected in a simple manner, there is usually introduced an additional DNA sequence coding for a selectable phenotype. There is still only a very limited number of such selectable marker genes for use in recombinant DNA technology of eukaryotic cells. Most of these available marker genes, such as, for example, the Herpes simplex virus type I thymidine kinase (Wigler et al., Cell 1 (1977) 223) or hypoxanthine phosphoribosyl transferase (Jolly et al., Proc. Nat. Acad. Sci. 80 (1983) 477) correspond to genes, or are highly related to genes, which are constitutively expressed in the majority of normal cells or are identical with such genes.

Therefore, these marker genes can only be used in special mutant cells which do not express the corresponding gene. A preferred marker gene on the other hand should not be expressed in the majority of mammalian cells or at least not be expressed in certain tissues and cell types, so that they can be used as selectable marker genes in recombinant DNA technology involving these cells.

Pawlink et al. have described the use of the CD24 cell surface antigen as a dominant selectable marker in retroviral mediated gene transfer (Journal of Cellular Biochemistry, Supplement 17 E, page 203, abstract S210). With this marker NIH-3T3 fibroblasts, BAF-3 pre-B cells as well as murine bone marrow cells could be labelled by retroviral infection and the labelled cells were detected by fluorescence activated cell sorting analysis. However, as the CD24 cell surface antigen is normally expressed on some mammalian cells, the use of this marker will be limited by the difficulty to differentiate between cells normally expressing the CD24 cell surface antigen and cells labelled with this marker.

Furthermore, it has been found that the CD24 cell surface antigen, following the heterologous expression, is presented at the cell surface to a little extent only.

It was therefore the object of the invention to provide a process for marking eukaryotic cells, with the use of cell surface receptors, by means of which process the cell surface receptors are presented to a large extent at the cell surface, whereby the sensitivity of the selection and of the detection of marked cells can be increased.

This object is accomplished by a process of marking a eukaryotic (mammalian) cell by expressing in this cell a nucleic acid, the nucleic acid encoding a cell surface receptor, and by presenting the receptor at the cell surface, the process being characterized by the use of a nucleic acid in which the region encoding the intracellular domain of the receptor is completely or partly deleted, or modified so that the receptor presented at the surface carilot effect any signal transduction after binding to its binding partner.

Preferably, the intracellular domain is completely deleted, or individual nucleotides are modified.

Preferably, there is used the nucleic acid encoding the NGF-, CD24- or the LDL receptor.

The sequence of the human NGF receptor, which will be referred to hereinafter as "low affinity nerve growth factor receptor, LNGFR", is described in D. Johnson, Cell 47 (1986) 545–554. Preferably, there is used a nucleic acid in which the DNA region encoding the amino acids 245 (beginning with nucleotide 930) to the C-terminus has been deleted (cf. SEQ ID NO:1).

In SEQ ID NO:1 the extracellular domain is coded by the nucleotides 114 (ATG)—863, the transmembrane domain is coded by the nucleotides 864–929, and the intracellular domain is coded by the nucleotides 930–1394 (Reddy et al., Molecular Brain Research 8 (1990) 137–141)

For the deletion of the intracellular domain it is possible to delete the complete domain or only a functional part so that the receptor presented at the surface cannot effect any signal transduction after binding to its binding partner. For example, it is possible to delete the nucleotides 943–1512 by restriction with PvuIII and SstI.

The nucleic acid can be introduced in the target cell, for example, via a viral vector (preferably, retrovirus) by means of lipofection or electroporation.

A further subject-matter of the invention is a DNA, which encodes a modified LNGFR and which is illustrated in SEQ ID NO 1, as well as a eukaryotic cell containing such a nucleic acid.

A nucleic acid of this type can be used to express a so modified cell surface receptor, and to present the receptor at the cell surface in such a way that the receptor can be used as a selectable marker for transfected eukaryotic cells.

The DNA encoding receptor or a derivative thereof will be introduced into a eukaryotic expression vector by methods known in the art. Suitable expression vectors are known to a person skilled in the art, preferably are used retroviral vectors. Also other viral vectors according to the state of the an can be used for the transfer of the receptor DNA (e.g. herpes viruses, adeno-viruses, vaccinia viruses). With a certain type of retrovirus, so-called double copy vectors (Yu et al., Proc. Natl. Acad. Sci. 83 (1986) 3194–3198), a high frequency of rearranged provirus and a significantly lower virus titer have been observed. XSN vector viruses (BioTechniques 7 (1989) 980–990) are preferred.

The recombinant eukaryotic expression vectors are then introduced into a eukaryotic host cell, either alone for a gene marking protocol, or in combination with a further DNA to be transduced, but which has no selectable phenotype. The introduction of the DNA into the host cell is accomplished by methods for viral infections known in the art. In addition, the transfer of the receptor gene can also be achieved by utilizing non-viral transfer methods (e.g. eleceroporation, liposomal transfer, calcium precipitation). Cells containing the exogeneous DNA can then be recognized by their ability to produce a receptor at high levels. Recombinant eukaryotic cells controlling a DNA according to the present invention can even be more easily detected by their ability to produce a derivative of the receptor.

The receptor label of the eukaryotic cells obtained as described above allows an easy selection and separation of such cells by using antibodies which bind to the receptor used. Such antibodies are known in the art and described, for example, by A. Ross et al. (Proc. Natl. Acad. Sci. 81 (1984) 6681–6685, EP-A 0 202 055). Furthermore, antibodies to the receptors can be obtained by methods known in the art by immunizing an animal with a protein encoded by DNA according to the present invention and isolating the antibodies from the serum of the immunized animals, or by fusing spleen cells of the immunized animals with immortal cells, such as, for instance, a murine myeloma cell line, to obtain monoclonal antibodies. These antibodies can be labelled by methods known in the art (such as are described, for example, in J. H. Peters, Monoklonale Antikorper, Springer Verlag, 2nd edition, 1988, pages 285 to 315). Suitables labels will be enzymes, fluorescent or chemiluminescent dyes.

It is possible to isolate the marked cells by immunoselection, by introducing such a nucleic acid into a eukaryotic cell. To thus end, the transfected cells are identified, selected with a marked antibody binding specifically to the receptor employed according to the invention, and isolated by being split off the antibody/cell complex.

By using an immobilized antibody instead of a marked (labelled) antibody, transfected cells can be selected. Therefore, the solid phase with the immobilized antibody against receptor is used as a matrix in affinity chromatography. After separation of non-transfected cells not expressing receptor, bound cells are, for example, cultivated and then expanded on petri dishes overnight.

The processes as described above will be especially important as diagnostic tools for the identification of cells introduced into a mammalian organism by gene therapy protocols. For some applications, such as, for example, bone marrow transplantation, it will be of diagnostic value to differentiate between cells originating from bone marrow transplantation and cells derived from residual cells of the host. In this case, bone marrow cells containing DNA encoding receptor are transplanted to provide these cells with a cell surface label. Preferably, progenitor or stem cells which were enriched according to the state of the art (e.g. immobilized anti-CD34 antibodies) containing the gene according to the invention will be transplanted. After transplantation, cells, especially eventually arising tumor cells, can be differentiated as being derived from the transplanted cells or residual cells of the host organism.

A further embodiment of the present invention is therefore the use of the process for immunoselection of transfected cells according to the present invention for the diagnostic identification of cells, which had been labelled by introduction of a DNA encoding receptor, especially of a DNA according to the present invention.

The main application of the marking of blood cells/bone marrow cells with the described modified receptors will be the monitoring of cells from autologous and also from allogenic transplants. In the treatment of leukemias and lymphomas, it is often necessary to treat the patients with sublethal doses of cytostatic pharmaceuticals or with comparable doses of irradiation or with combinations thereof. To restore bone marrow function either autologous bone marrow which is explanted before treatment will be reimplanted into the patients or allogenic genic marrow from a HLA matching donor will be implanted.

In the case of autologous bone marrow transplantation contamination of tumor cells in the reimplanted material might lead to a tumor relapse. Purging methods to purify the marrow from tumor cells (clonogenic tumor cells) are employed but these techniques are not reliable at this time. In the case of a relapse it is of course not possible to distinguish between these potentially contaminating tumor cells and a relapse caused by residual cells after treatment. In the case of allogenic bone marrow transplantations the rejection of the allogenic marrow is the main problem. Purging techniques are described in Areman E. M. et al: Bone Marrow and Stem Cell Processing: A Manual of Current Techniques, F. A. Davies Co., Philadelphia (1992), which is incorporated herein by reference.

The invention further comprises a method for the preparation of a hematopoietic cell preparation (i.e. bone marrow or mobilized peripheral blood progenitor cells and/or stem cells), wherein said cells are marked with a cell surface receptor and whereby said cell preparation is substantially free of clonogenic tumor cells, by purging using cytotoxic agents or irradiation, transducing said cells with a nucleic acid which encodes a cell surface receptor and, preferably, in which the region encoding the intracellular domain has been completely or partly deleted or modified in such a way that the domain can essentially no longer effect any signal transduction, and separating said transduced cells from non-transduced cells. The separation is preferably accomplished by incubating said cells with an antibody against the receptor immobilized prior to or after incubation, separating the cells immobilized by the antibody from unbound cells, and isolating the hematopoietic cell preparation by cleaving the antibody-receptor binding.

If after autologous transplantation the transplanted cells are marked with a gene and consequently with the gene product derived thereof which is not common to these cells it is possible to trace these cells directly after transplantation and in the case of relapse to differentiate between tumor cells derived from the transplanted material and residual tumor cells. This knowledge will lead to a very early definition of the further treatment based on the source of relapse. Besides this diagnostic purpose, gene marking in autologous transplantations will also allow to monitor and compare the efficacy of different purging methods in relatively small patient groups.

For autologous and, preferably, allogenic transplantation the main field of application will be the monitoring of rejection of transplanted cells.

The clinical protocol will contain the following steps:
a) Explantation of patient cells.
b) Purging of explanted cells according to the known art.
c) Transduction of the patient cells with a vector containing the modified receptor gene according to this invention.
d) Facultatively expansion of the patient cells under selective conditions, e.g. with G418 utilizing the expression of the neomycin resistance gene coded on the vector containing the modified receptor gene.
e) Immunoselection of the marked cells which express the modified gene and present the receptor on the surface of the cells.
f) Reimplantation of the enriched and marked cells into the patient.
g) Monitoring blood/marrow samples of the patient for the marking gene by FACS analysis or ELISA techniques.

The invention further comprises a method for the immunoselection of transfected cells, by introducing into said cells a nucleic acid which codes for a cell surface receptor in which the region encoding the intracellular domain of the receptor has been completely or partly deleted or modified in such a way that the receptor presented at the surface cannot, after binding to its binding partner, effect any signal transduction, identifying the transfected cells by incubation of the cells with a marked antibody which binds specifically to said receptor, and recovering the cells by cleavage from the antibody/cell complex.

The invention further comprises a method for the immunoselection of transfected cells, by introducing into said cells a DNA which codes for a cell surface receptor in which the region encoding the intracellular domain of the receptor has been completely or partly deleted or modified in such a way that the receptor presented at the surface cannot, after binding to its binding partner, effect any signal transduction, incubating the cells with an antibody against the receptor immobilized prior to or after incubation, separating the cells immobilized by the antibody from unbound cells, and isolating the cells by cleaving the antibody-receptor binding.

A large number of studies have demonstrated that retroviral vectors are an efficient tool for transfer of exogenous DNA into somatic cells[1]. In the mouse hematopoietic system, efficient gene transfer and expression has been achieved into both progenitors and pluripotent stem cells, in vitro as well as in vivo. Lower levels of gene transfer have been obtained in canine and human hematopoietic progenitors in culture, in which significant levels of expression of the transduced genes have been demonstrated (reviewed in [2]). Retroviral-mediated gene transfer is currently utilized in gene therapy protocols for treatment of inherited and acquired diseases, such as adenosine deaminase-deficient (ADA[31]) severe combined immunodeficiency (SCID) and advanced cancer (reviewed in [3]). Although significant effort is being devoted to optimize procedures for purification of human hematopoietic stem cells and finding efficient conditions for gene transfer and expression, peripheral blood lymphocytes (PBLs) are still considered the safest cellular delivery vehicle for human gene therapy.

A number of different retroviral vectors have been engineered and used for gene transfer into human hematopoietic cells, all based on the Mloloney murine leukemia virus (MoMLV) backbone. Usage of different promoters driving expression of the gene of interest, and the position of these sequences with respect to the viral transcription unit, were some of the parameters taken into account in generating alternative vector designs[4][5][6] Some of these vectors were used to transduce human lymphoid cells under different conditions. Human tumor-infiltrating lymphocytes (TILs) were transduced with the N2 retroviral vector, carrying a neomycin phosphotransferase (Neo) gene, and retained normal phenotypic and functional characteristics in vitro[7][8]. Transduced cells were recovered from tumor sites up to 64 days after in vivo cell administration to melanoma patients[9]. Gene transfer was obtained in both CD4+ and CD8+ human T-cell subsets derived from TILs and PBLs[10]. A retroviral vector for expression of a functional CD18 gene, driven by viral LTR promoter, successfully transduced lymphocytes from patients affected by leukocyte adhesion deficiency (LAD), and led to correction of LAD in vitro. Expression of human ADA driven by an ADA promoter into a double-copy vector[6] in PBLs obtained from patients affected by ADA[31] SCID also led to correction of the enzyme deficiency, allowing reconstitution of immune functions[12][13]. Finally, retroviral constructs for overexpression of HIV structural RNA sequences (transducedacting responsive element, TAR, and Rev-responsive element, RRE), driven by a RNA polymerase III promoter, were successfully introduced into a T-lymphoid cell line, inducing partial intracellular immunization against HIV[14][15]. Although in all these cases retroviral vectors were shown to transduce human lymphoid cells and express the transferred genes, no attempt has yet been made to directly compare the different vector designs for stability, efficiency of gene transfer, and expression of the transduced gene.

The human low affinity nerve growth factor receptor (LNGFR) is not expressed on the majority of human hematopoietic cells, thus allowing quantitative analysis of the transduced gene expression for each vector and each cell target by immunofluorescence analysis, even at single cell level. Different human hematopoietic cell lines of myeloid and lymphoid origin, as well as normal peripheral blood mononuclear cells (PBMC), were transduced with four vector constructs and analyzed for stability and number of viral integrations and LNGFR expression, at both RNA and protein level. FACS analysis of transduced T-cell lines and clones for coexpression of LNGFR and cell surface markers was carried out to study gene expression into specific T-cell subpopulation. Under appropriate, high efficiency infection conditions, all retroviral vectors could transduce a T-cell population of the normal immune repertoire. Therefore, according to the invention, LNGFR (in its truncated form without the intracellular domain, or in its (essentially) not modified form) is a preferred marker for cell marking, by transfecting the cells with a nucleic acid coding for LNGFR. For transfection there are used, for example, vectors such as retroviral vectors or also naked DNA, e.g. with liposomes as transfecting agent. LNGFR marker is preferably used for marking of cells of the hematopoietic system, especially of hematopoietic stem cells. Especially preferred is the use for marking in gene therapy and purging methods.

Efficient retroviral vector gene transfer into hematopoietic stem cells still remains the prime goal of gene therapy for many congenital and acquired disorders. As vehicles, retroviral vectors are currently the safest and most effective tool for transfer and expression of exogenous DNA into human hemato-lymphopoietic cells. Actually, all the approved clinical protocols for gene transfer in marrow or blood cells rely on retroviral vectorsl[1,3]. Although the ideal target cell is represented by the pluripotent stem cell, there is no conclusive evidence about the ability of retroviral vectors to transduce such cells at adequate efficiency, and maintain stable gene expression in their progeny. The results of in progress clinical protocols based on bone marrow gene transfer may clarify these problems [1,3,30].

Clearly, gene transfer can be more easily achieved into peripheral blood lymphocytes, a potential alternative to bone marrow cells, at least for congenital and acquired disorders of the immune system. However, for this purpose, it is necessary to define what proportion of PBLs needs to be transduced in order to represent the whole immuno repertoire, and whether this can be stably maintained in vivo, both necessary prerequisites for a gene transfer procedure to be of therapeutical relevance. For this purpose, the efficiency of gene transfer and vector design, which affects both persistence and levels of gene expression, are crucial factors.

The overall efficiency of gene transfer into human PBLs was strictly dependent upon the infection protocol. Limited cell expansion by short-term activation in vitro of lymphocytes, followed by gene transfer into PBLs by exposure to producer cell supernatants resulted in a limited proportion of G418-resistant cells (approximately 1% per infection cycle), with additional variability introduced by the titer of vector supernatants. Efficiency of gene transfer can be increased by more extended in vitro expansion of target cells.

The analysis of the repertoire of Vβ usage in the population of PBLs, after three cycles of PBLs infection by vector-containing supernatants, followed by selection of transduced cells by G418, produced an intact repertoire as compared to the original control population of untransduced/unselected lymphocytes. These data show that limited expansion of target cells and utilization of vector-containing supernatants produce adequate gene transfer, independently of the relatively low frequency of gene transfer, at least when the vector supernatants have good viral titers (>5× 10$^5$). However, low viral titers in vector supernatants produced limited Vβ repertoires. This was confirmed by Southern blot analysis of the TCR-β chain rearrangement, that showed oligoclonal pattern in the transduced/selected population. This limitation was circumvented by co-culture of PBLs with irradiated vector-producing cells. Independently of viral titer this gene transfer procedure is significantly more effective, by at least one order of magnitude. Taking advantage of the high efficiency of gene transfer by co-cultivation and the expression LNGFR on transduced lymphocytes, a simple protocol was deviced involving cultivation and immunoselection that allows production of homogeneously transduced cells.

Since co-culture protocols are still considered unsafe for clinical use, co-ulture conditions were designed in which vector-producing cells and PBLs were kept separated by a porous membrane, which allows virus passage while avoiding cell-to-cell contact. This approach offers some advantage when compared to supernatant infection.

Double fluorescence analysis of G418-selected T-cells for co-expression of LNGFR and different T-cell surface markers showed similar susceptibility of all the tested subpopulations with apparently equal efficiency of gene transfer. Furthermore, we obtained sporadic, though conclusive evidence of gene transfer into immature, CD4+/CD8+ cells. We have previously shown retroviral vector-mediated gene transfer into T-cell progenitors preceding TCR rearrangement[13]. The data of the invention show that retroviral infection of PBMCs allows gene transfer into circulating progenitors at low but detectable frequency. This may be an additional advantage of gene transfer protocols involving short term in vitro culture and limited expansion of target lymphocytes.

Further, the impact of vector construct on efficiency of gene transfer and expression is analyzed. In the vector constructs utilized, the reporter gene was alternatively placed within the retroviral transcription unit under the control of internal SV40 or HSV-TK promoters (NSV-N and NTK-N vectors, respectively), under the MoMLV viral LTR (LNSN/SFCM), or outside the retroviral transcription unit under the control of the human ADA promoter (the "double-copy" vector DCN). The use of a receptor according to the invention as a reporter gene allowed the study of gene expression levels in different PBL subpopulations, with single cell resolution.

The viral titers obtained for different vectors in the selected producer clones were comparable, with the exception of the DCN producer cells which consistently yielded titers up to five-fold lower than those for the other three vectors, suggesting that the extra sequence in the viral LTR may reduce the transduction efficiency, probably by interfering with the reverse transcription/integration process. This is also reflected by the relatively high tendency of DCN to integrate as a rearranged provirus, which further reduces the overall gene transfer efficiency that can be obtained with this type of vector. Rearrangement of integrated proviruses was observed at negligilbe frequencies for the other three vectors.

Gene expression levels showed that vectors based on internal transcription units were the least efficient in terms of both mRNA accumulation and protein expression. The only exception was the very high level of transcripts generated by the SV-40 promoter within two different vectors (NSV-N and LNSN/SFCM) in the EBV-infected B-cell line RIM. This may be due to interaction action of EBV trans-activating proteins with the SV-40 enhancer. On the contrary, the vectors based on the MoMLV LTR and the human ADA promoter for expression of the reported gene worked very efficiently in all hematopoietic lines. Analysis of T-cell lines and clones gave essentially the same results. Both LNSN and DCN vectors were very efficient in directing high levels of gene expression in all T-cell subpopulations, including immature progenitors, and maintained these levels unaltered throughout a high number of passages.

In conclusion, the LTR-based retroviral vector is probably the most reliable and efficient for gene transfer and expression into human PBLs, whereas the DC design, although very good as far as gene expression is concerned, results in generally low gene transfer efficiency due to both the lower titer and the tendency to genornic rearrangement. This type of construct, however, could be the vector of choice when tissue-specific, inducible, or otherwise LTR-independent gene expression is a mandatory requirement, or else in tissues in which LTR inactivation might occur. Although we did not address this issue in the present study, human hematopoietic stem cells could be among these tissues, by analogy to what observed in the murine hematopoietic system.

The utilization of a gene coding for the cell surface molecule LNGFR or coding for a cell surface molecule in which the intracellular domain of the receptor has been completely or partly deleted or modified in such a way that the receptor presented on the surface cannot, after binding to its binding partner, effect any signal transduction, for retroviral vector-mediated cell marking clearly represents an important advantage over vectors utilized in previous gene marking experiments that utilize a marker gene, usually the NeoR gene, not expressed on the cell membrane. This type of vector would represent a potential advantage for in vivo preclinical and clinical studies of cell marking.

LTR, ψ: packaging signal)

Figure 5:
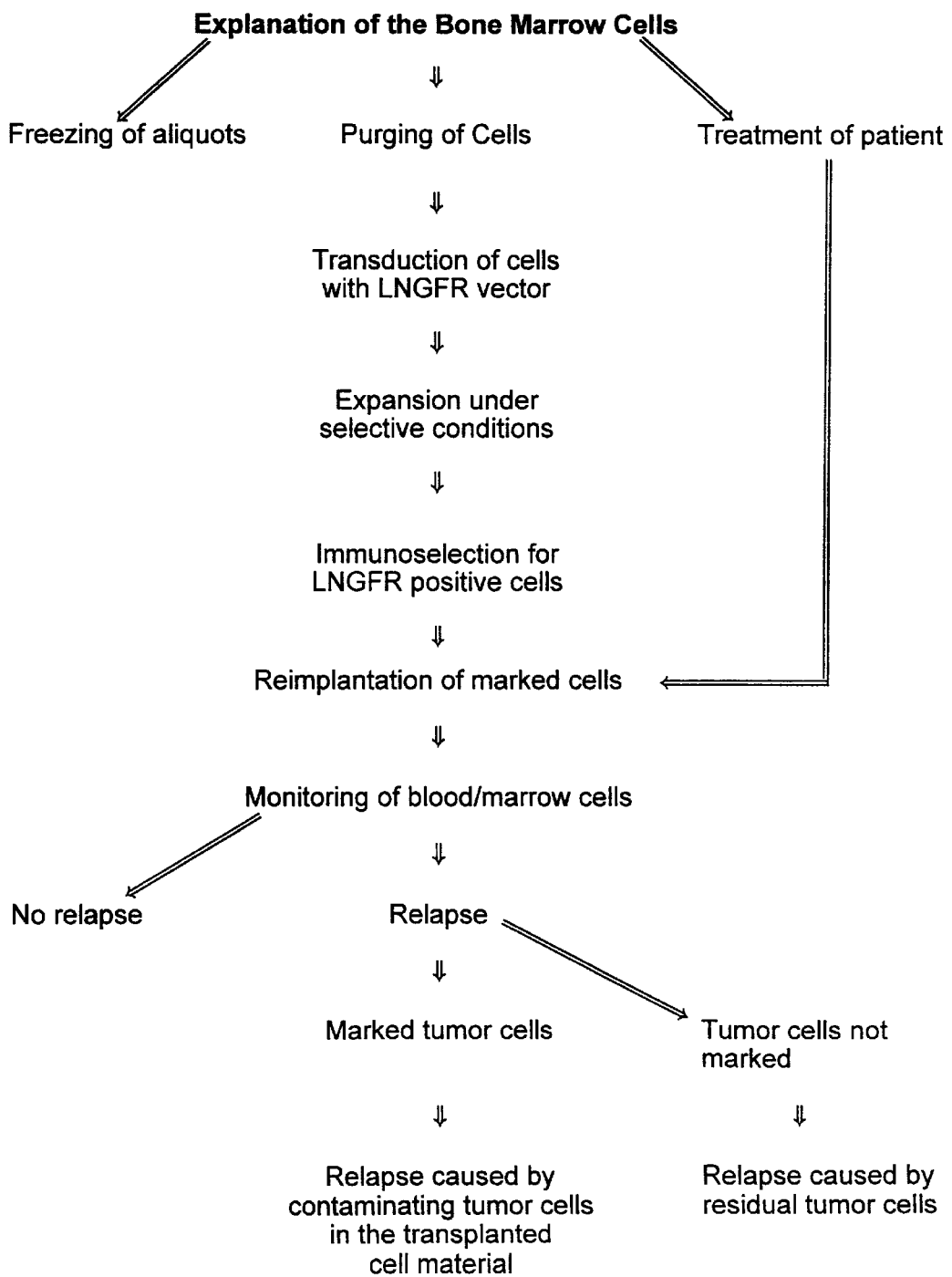

FIG. 5: A schematic flow diagram for the gene marking protocol is shown.

EXAMPLES

Example 1

Retroviral vectors

Different retroviral vectors for expression of LNGFR as a reporter gene were generated, using the full-coding 1.5 Kb Sst I fragment of the human LNGFR cDNA[16] or a truncated LNGFR cDNA without an intracellular domain (e.g. by restriction with PvuII and SstI). The NSV-N and NTK-N vectors were obtained by cloning the LNGFR cDNA into the unique Hind III and Bgl II sites of the NSV and NTK vectors, respectively. The NSV vector was derived from the original N2 vector[17] by insertion of the 0.4 kb Kpn I/Hind III fragment containing the SV40 early promoter enhancer and origin of replication into the unique Xho I cloning site. The NTK vector was also derived from N2 by insertion of the 852 bp Herpes Simplex Virus (HSV) thymidine kinase (TK) promoter.

The LNSN vector was constructed by insertion of the LNGFR cDNA into the Hpa I site of the LXSN vector[5].

In the DCN vector (double copy LNGFR) the LNGFR cDNA was cloned under the control of the 0.8 kb Ssp I/Nco I fragment of the human adenosine deaminase (ADA) promoter[18] into the Bgl II/Sna BI sites of the N2A retroviral vector/polylinker[6].

Quite similarly, it is possible to use in the NSV-N, NTK-N, LNSN and DCN vectors instead of the LNGFR cDNA a truncated LNGFR cDNA (ΔLNGFR).

Figure 3:
FIGS. 3 and 4: Different vector constructs. (L: leader sequence; EXTR: extracellular domain; T: transmembrane domain; INTR intracellular domain; black boxes.
Figure 3:
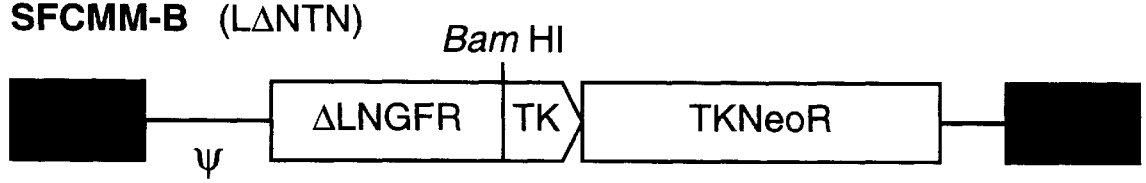
Figure 3:
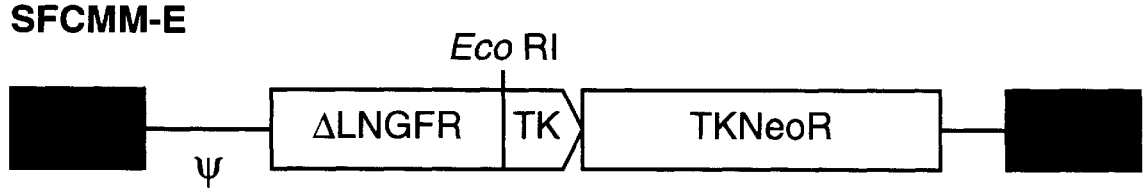
Figure 3:
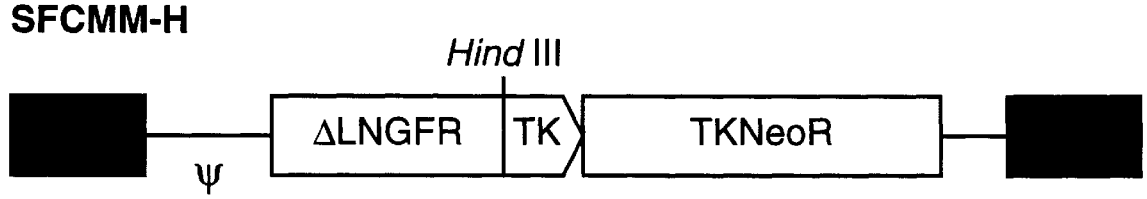
Figure 3:
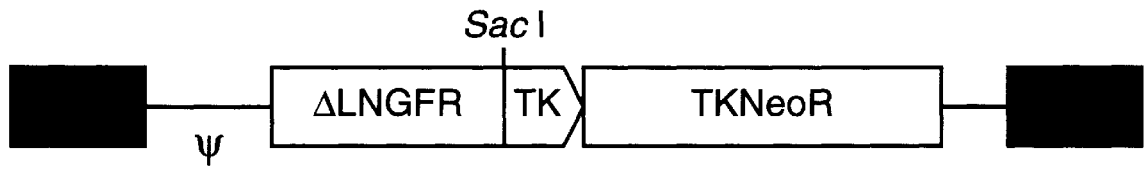
Figure 3:
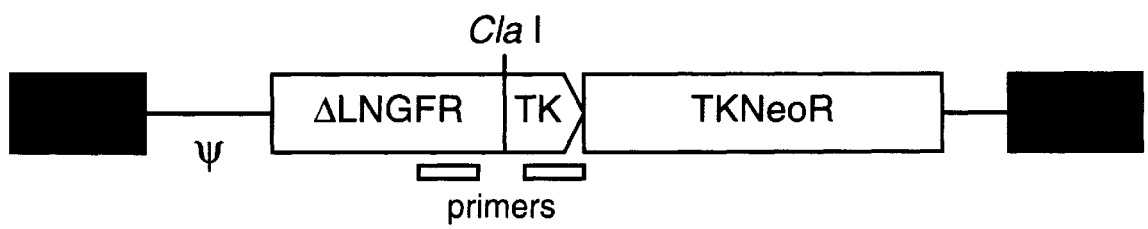
Figure 4:
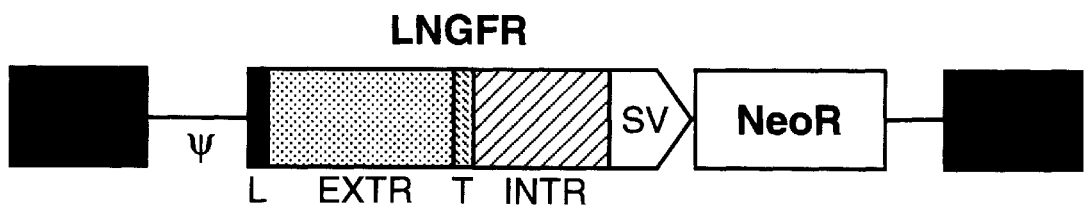
Figure 4:
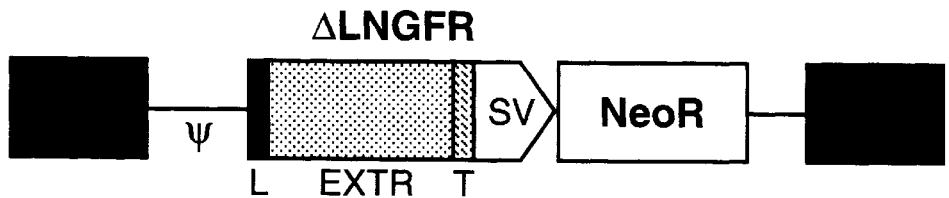

Different vector constructs according to the invention are shown in FIGS. 3 and 4.

Vector DNAs were converted to corresponding viruses by the transinfection protocol. Briefly, vector DNA was transfected into the ψ2 ecotropic packaging cell line[19] by standard calciumphosphate co-precipitation[20] 48 hrs after transfection, ψ2 supernatants were harvested and used to infect the amplotropic packaging cell lines PA317[21] for 16 hrs in the presence of 8 µg/ml polybrene. Infected PA317 cells were selected in DMEM (GIBCO, Grand Island, N.Y.) Supplemented with 10% FCS (Hyclone, Logan, Utah) and containing 0.8 mg/ml G418 (GIBCO), and then used to generate helper-free, virus-containing supernatants with titers ranging from $10^4$ to $5\times10^5$ cfu/ml. All vectors contain the gene NeoR gene coding for neomycin phosphotransferase, that confers in vitro resistance to the neomycin analogue G418.

Infection of hematopoietic cell lines

All cell lines described in this study, with the exception of RIM and J.M., were obtained from ATCC, and grown in RPMI 1640 (GIBCO) supplemented with 10% FCS. K562 and KG1 are myeloid cell lines, derived from chronic and acute myelogenous leukemias, respectively; Raji and Daudi are derived from two Burkitt's lymphomas; MOLT-4 is considered a stable T-cell leukemia (CD8$^+$); RIM is an EBV-transformed lymphoblastoid cell line; J.M. is a CD4$^+$/CD8$^+$ T-lymphoblastoid cell line; A875 is a human melanoma cell line expressing ~$10^6$ LNGFRs/cell.

$5\times10^5$ target cells were infected for 16 hrs with undiluted viral supernatants containing 8 µg/ml polybrene, grown for additional 24 hrs in complete medium and then selected in the presence of the previously determined dose of G418 (0.5 to 1.5 mg/ml). Further analyses were carried out on bulk cultures of G418-selected cells.

Infection of human PBMC

Peripheral blood mononuclear cells (PBMC) were obtained from healthy donors by Ficoll-Hypaque (Pharmacia, Uppsala, Sweden) gradient separation and grown for 72 hrs under phytohemagglutinin (PHA) and human recombinant interleukin2 (hu-rIL2) stimulation (2 µg/ml of purified PHA, Wellcome, Labs., Dartford, UK; 100 U/ml of hu-rIL2, Roche, Nutley, N.J.). Viral infection was carried out by exposure of stimulated PBLs to a cell-free viral stock for 6 hrs in the presence of polybrene (8 µg/ml). 48 hrs after infection, PBLs were selected in RPMI 1640 supplemented with 2 mM L-glutamine, 1% non-essential aminoacids, 1% Na pyruvate, 5% human serum (HS) and 100 U/ml hu-rIL2 (complete medium), containing 0.4 mg/ml G418. Cell density was maintained constant ($5\times10^5$ cells/ml) during 2 wks of G418 selection. Retroviral-transduced human T-lymphocytes were also cloned in Terasaki plates at different cell concentration (1–$10^3$ cells/well) in complete medium containing 0.4 mg/ml G418, in the presence of irradiated human PBLs as feeder cells.

In order to improve the retroviral infection efficiency, human PBLs were co-cultivated with virus-producing cell for 48–72 hrs in complete medium. Co-cultivation was also carried out in Transwell plates (Costar, Cambridge, Mass.) to prevent cell-to-cell contact. $3\times10^5$ producer cells were seeded in the cluster plate wells of 6-well dishes and incubated at 37° C. O/N. $5\times10^5$ stimulated PBLs were added into the Transwells and grown for 48–72 hrs in the presence of 8 µg/ml polybrene.

Retroviral-transduced cells were analyzed by flow cytometry for receptor expression and expanded for further analyses.

DNA analysis

High molecular weight DNA was obtained from cells by standard phenol/chloroform extraction[20], digested to completion in 5 µg aliquots with appropriate restriction enzymes (GIBCO-BRL), electrophoresed in 0.8% agarose gels at 1.5 V/cm in tris-acetate-EDTA buffer, transferred to a nylon membrane (Hybond-N, Amersham, Buckinghamshire, UK) by Southern capillary blotting[20] and hybridized to $10^7$ dpm of [$^{32}$P]-labeled probe.

DNA analysis—Southern blot

Probes:

1) fragment of pSV2-neo and
2) fragment containing TCR-β-constant region

DNA probes were a 1.2 Kb Hind III/Sma I fragment of pSV2-neo [22] and the Hinc II 3' fragment of the YTJ-2 cDNA clone, containing the human TCR-β constant region[23]. Filters were washed under high stringency condition and exposed to Kodak X-AR 5 films at −70° C.

RNA analysis—Northern blot

Probes:

1) fragment ov pSV2 neo and
2) fragment of LNGFR cDNA

Total cellular RNA was extracted by the guanidine-isothiocyanate technique[24] and selected for poly(A)$^+$ by oligo (dT)-cellulose chromatography[20]. 5 µg of poly(A)$^+$ RNA were size-fractionated on 1% agarose-formaldehyde gel, transferred onto nylon membrane by Northern capillary blotting[25], and hybridized, washed and exposed as described for Southern blots. DNA probes were a 1.2 Kb Hind III/Sma I fragment of pSV2-neo and the 1.5 Kb Sst I fragment of the LNGFR cDNA[16].

CELL SURFACE PHENOTYPE

Expression of LNGFR monitored by flow cytometry using 1) antihuman LNGFR with fluorescein label and
2) PE conjugated anti-human MoAbs.

Cell surface expression of LNGFR was monitored by flow cytometry utilizing the murine antibodies human LNGFR monoclonal antibody 20.4 (ATCC) with an indirect fluorescence labelling method. Cell surface phenotype of T-lymphocytic lines and clones was determined by flow cytometry using PE-conjugated anti-human-CD4 (T4), CD8 (T8), CD5, B4, CD25R, Leu7, CD34 monoclonal antibodies (MoAb) (Coulter Immunology, Hialeah, Fla.). Briefly, $5\times10^5$ cells were stained with 100 µl of diluted antibodies at 4° C. for 30 min., washed twice in medium without FCS and resuspended in 0.5 ml of PBS for FACS analysis or in 100 µl of diluted FITC-conjugated secondary antibody. Double-staining analysis was performed by sequential incubation of FITC- and PE-conjugated antibodies.

ANALYSIS OF TCR Vβ-CHAIN USAGE VIA PCR

Total RNA was extracted from PBL and T cell lines using GTC, [26] reverse transcribed into cDNA using oligo dT and dG tailed, [27] one twentieth of the obtained DNA was subjected to PCR by the use of Vβ-Cβ specific oligonucleotides, [28] and to anchor PCR utilizing a Cβ-specific oligonucleotide (5'-TGCTGACCCCACTGTCGACCTCCTTCCCATT-3') (SEQ ID NO:2), as described in ref 27. PCR amplification cycles were performed at: 94° C. for 45", 57° C. for 45", and 72° C. for 1'. The amplified product was gel purified and cloned into bluescript plasmid vector. Cβ positive colonies were replicated onto different plates and transferred to nitrocellulose filters and hybridized to Vβ-specific oligonucleotides[28, 29] under the following conditions: 6× SSC, 1% blotto, 0.1% SDS and 5 mM EDTA at 42° C. for 3–6 hrs, washed for 1 hr at the same temperature in 6× SSC and exposed for 6–12 hrs to an X-ray film at room temperature.

Results

Generation of recombinant retroviruses for expression of the LNGFR

Figure 1:
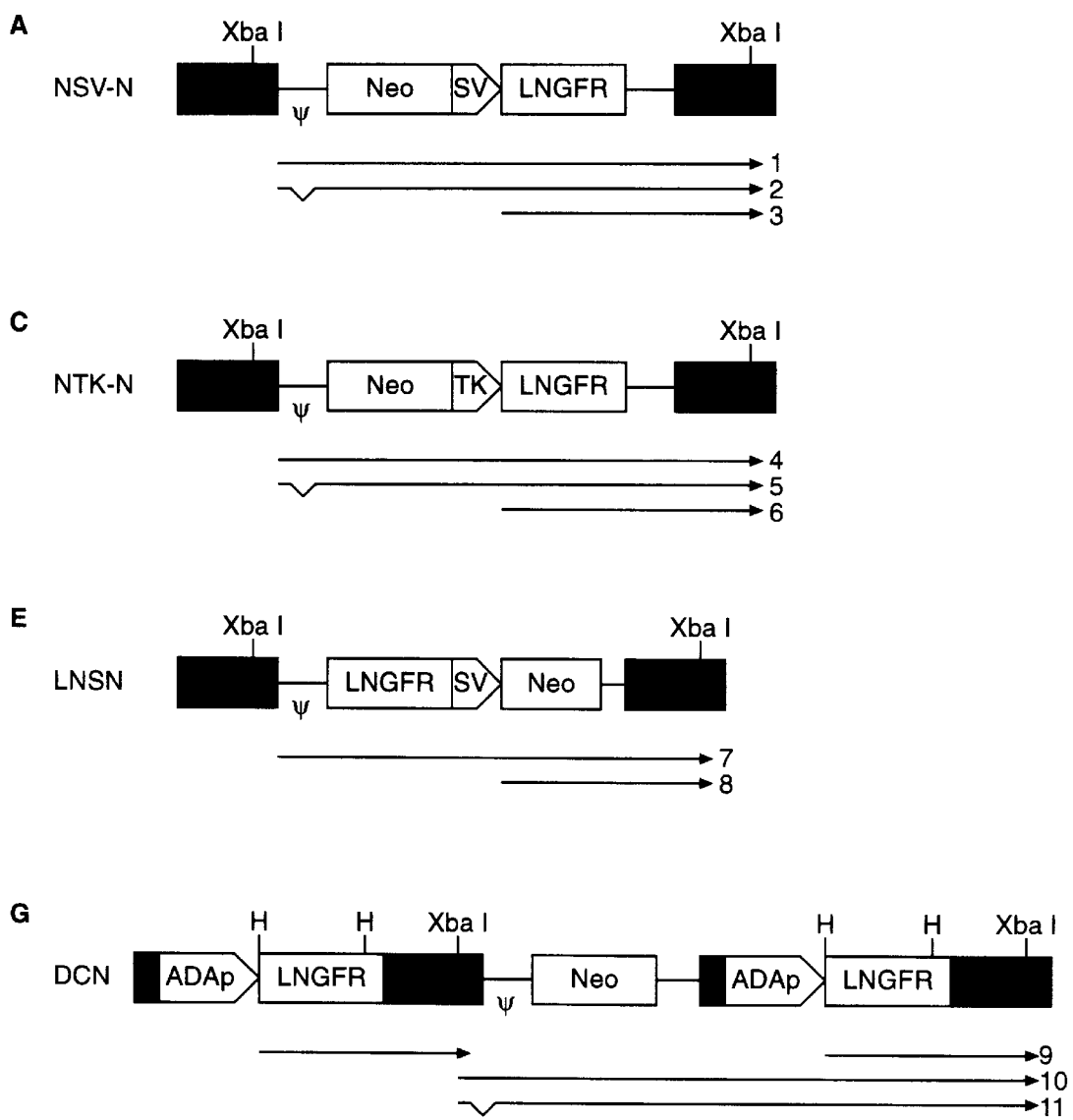
FIGS. 1A–1G: Retroviral vectors for LNGFR expression (A,C,E,G). Schematic maps of integrated NSV-N (A), NTK-N (C), LNSN (E) and DCN (G) proviral genomes are shown, indicating the SV40 (SV), HSV-TK (TK) and human ADA (ADAp) internal promoters. Black boxes denote LTR sequences. Xba I and Hind III (H) restriction sites are indicated. The RNA species originating from each vector are represented by numbered arrows on the maps.

Different retroviral vector constructs for LNGFR expression were developed and utilized for generation of virus-producing cell lines. The NSV-N (FIG. 1A) and NTK-N (FIG. 1C) constructs are based on internal promoters, driving the LNGFR cDNA, i.e. the SV40 early promoter and HSV-TK promoter, respectively. In the LNSN vector (FIG. 1E), the LNGFR gene is expressed from the viral LTR. In the DCN construct (FIG. 1G), the LNGFR cDNA is under the control of the human ADA promoter, within the U3 region of the 3' LTR. The SFCM constructs contain a truncated LNGFR gene, wherein the intracellular domain is deleted (ΔLNGFR). After infection of target cells, the transduced gene is duplicated and transferred to the 5' LTR [6], thus generating a provirus containing two copies of the ADA-LNGFR minigene. All vectors carried the NeoR gene, under the control of either the viral LTR (NSV-N, NFK-N and DCN) or the SV40 early promoter (LNSN and SFCM).

The vectors were utilized to transduce the LNGFR gene (and the truncated LNGFR gene respectively) into human hematopoietic cell lines of different lineages and into human PBLs, and they are all able to 1) transduce human target cells,
2) integrate and form intact proviruses, and
3) express the reporter gene.

The viral titer of the amphotropic producer cell lines ranged from $1\times10^4$ to $5\times10^5$ cfu/ml for NSV-N, NTK-N, LNSN and SFCM vectors, and from $5\times10^3$ to $1\times10^4$ cfu/ml for DCN.

Molecular analysis of viral integration in human hematopoietic cell lines

For the initial screening of the different vectors, a number of tumor cell lines of the hematolymphopoietic origin were utilized as target cells for gene transfer. Two myeloid cell lines (K562 and KG1), two Burkitt's lymphomas (Raji and Daudi), one EBV-transformed lymphoblastoid cell line (RIM), and two T-lymphoblastoid cell lines (MOLT-4 and J.M.) were transduced with the four retroviral vectors and selected in the presence of G418. Molecular analysis of retroviral integrations was carried out by Southern blotting to detect the size of integrated virus and the copy number (about 1 to 5 copies/cell). Genomic DNAs were digested with Xba I, which cuts in both 5' and 3' LTRs of all vectors (FIG. 1), allowing detection of the size of integrated proviruses, and with Bgl II, which cuts only in genomic DNAs, allowing estimation of the number of integration sites. XBa I- and Bgl II-digested DNAs were hybridized to NeoR and LNGFR genes specific probes sequentially.

Figure 2:
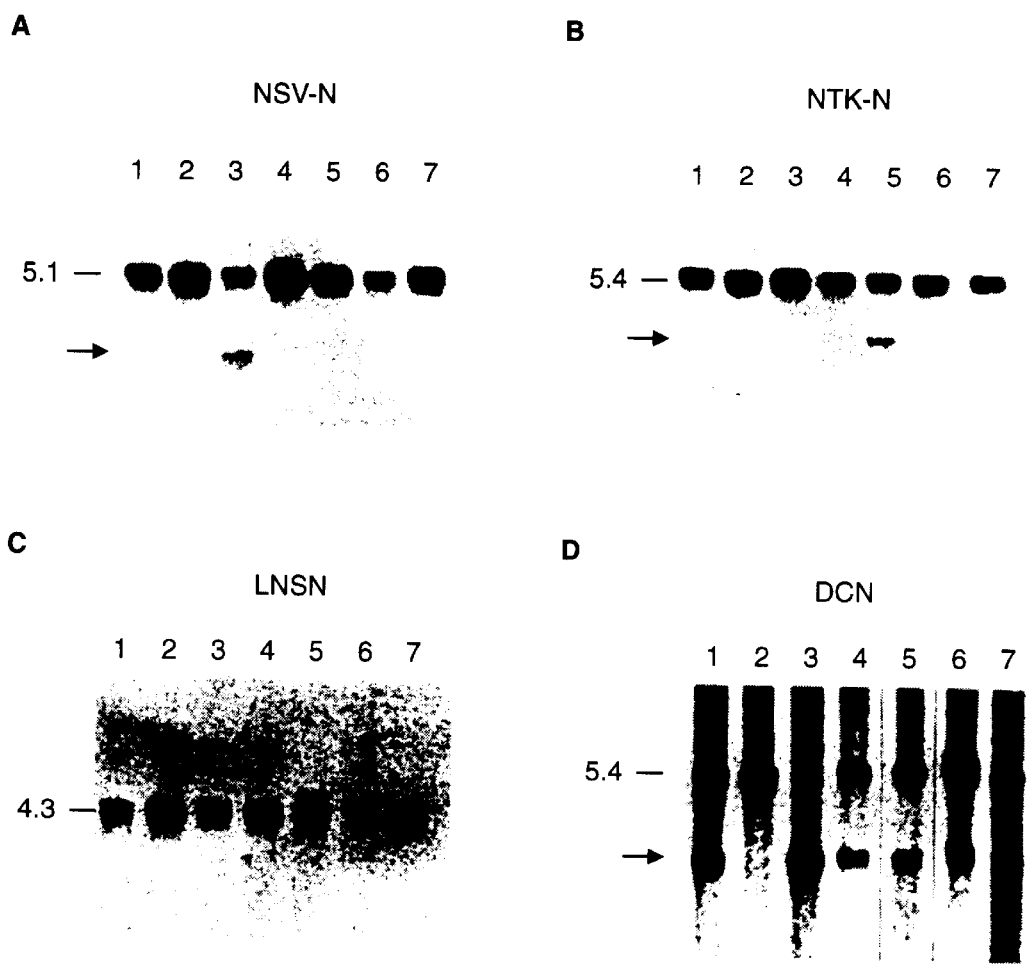
FIGS. 2A–2D: Southern blot analysis of integration of the four retroviral vectors (A-D) in Xba I digest of DNA of K562 (1), KG 1 (2), Raji (3), Daudi (4), RIM (5), MOLT-4 (6) and J. M. (7) cell lines, hybridized to the Neo probe. Bands corresponding to intact, integrated proviruses are indicated, together with their molecular weight (in kb). Rearrangement bands are indicated by arrows.

Integration of the NSV-N vector generated a single Xba I band of the expected 5.1 kb size, corresponding to an intact provirus, in all the G418-selected cell lines (FIG. 2A). In the Raji cells an additional band of smaller size was observed, indicating integration of a rearranged provirus (FIG. 2A, lane 3).

Similarly, Xba I digestion generated a single band of the expected 5.4 kb size in the DNAs from all the NTK-N-infected cell lines (FIG. 2B). An additional band, probably due to the presence of a rearranged provirus, was detected only in the RIM sample (FIG. 2B, lane 5). A single band of 4.3 kb was seen in all samples transduced with the LNSN and SFCM vector with no evidence of viral rearrangements (FIG. 2C). On the contrary, the pattern of viral integrations in DNAs from cells infected with DCN was characterized by frequent rearrangements (FIG. 2D). All the DCN-transduced cell lines showed the presence of a 5.4 kb band, corresponding to the intact provirus, but an additional band of 3.2 kb was detected in all but one (KG1) cell lines. The relative proportion of the two bands was variable in the analyzed samples, ranging from predominance of the intact provirus (MOLT4, FIG. 2D, lane 6) to prevalence of the rearranged one (Raji, FIG. 2D, lane 3). Repeated infections with the same retroviral stock indicated that the proportion between intact and rearranged provirus is a random, non-cell-specific event.

As observed for the cell lines transduced by all other vectors, the Bgl II pattern showed that DCN infection generated polyclonal integration in all cell lines.

In order to investigate the nature and the mechanism responsible for the generation of rearranged provirus, we carried out additional digestions of genomic DNAs with Hind III, which cuts twice in the ADA-LNGFR minigene, followed by hybridization with the LNGFR probe. The comparative analysis of Xba I and Xba I/Hind III restriction patterns with both probes indicated that the 3.2 kb band corresponded to a rearranged provirus lacking the ADA-LNGFR minigene from both LTRs. Defective proviruses were also detected at high frequency during selection of the DCN producer cell lines. The clone used in all our experiments harbored only the intact provirus, indicating that generation of defective proviruses occurs during integration in the target cells, and is not due to defects of the producer cell line.

In summary, infection of all cell lines with NSV-N, NTK-N, LNSN and SFCM gave rise to G418-resistant populations carrying low copy numbers of mostly unrearranged proviruses, whereas infection with DCN vector generated a common rearranged provirus at high frequency, most likely derived by the loss of the ADA-LNGFR minigene from the 3' LTR of the retroviral vector during the integration process. This problem may be due to the size and nature of the inserted gene in the viral LTR, similar limitations with other "double-copy" vector constructs were not observed [12–14].

Vector-mediated LNGFR expression in human hematopoietic cell lines

Expression of LNGFR transduced by the different retroviral vectors was evaluated at both protein and mRNA levels. Cell surface expression of LNGFR in the G418-selected cell lines was quantitatively analyzed by flow cytometry with an anti-LNGFR MoAb. The results are summarized in table 1. Most of the NSV-N- and NTK-N-transduced cell lines showed a low-medium level of surface LNGFR, expressed as relative mean fluorescence (<100 arbitrary units). High expression of LNGFR (202 a.u.) was observed only in the EBV-infected RIM cell line transduced by NSV-N. LNGFR expression was not detected in the NTK-N-transduced MOLT-4 cell line, although no rearrangement of the previral genome was detected in Xba I-digested genomic DNA (FIG. 2B, lane 6). Repeated gene transfer by this vector in the same cell line gave consistently negative results.

All cell lines transduced with LNSN and SFCM retroviral vectors expressed LNGFR at medium-high levels (50–200 a.u.) (table 1).

TABLE 1

FACS analysis of LNGFR expression in human hematopoietic cell lines transduced by the four retroviral vectors

| Cell line | Retroviral Vector | | | |
|---|---|---|---|---|
| | NSV-N | NTK-N | LNSN[c] | DCN[b] |
| K562 | +[a] | + | +++ | ++ |
| KG1 | ++ | ++ | ++ | +++ |
| RAJI | ++ | + | ++ | − |
| DAUDI | ++ | ++ | +++ | +++ |
| RIM | +++ | ++ | ++ | +++ |
| MOLT-4 | + | − | ++ | ++ |
| J.M. | ++ | ++ | +++ | +++ |

[a]Quantitative expression of LNGFR was scored as: −, 0 arbitrary units (a.u.) of relative mean fluorescence intensity, +, 0–50 a.u., ++, 50–100 a.u., +++, 100–200 a.u. The relative mean value of A875 melanoma cell line, expressing ~$10^6$ receptors/cell, was 190 a.u.
[b]FACS profiles of K562, Daudi, RIM, and J.M. were biphasic, and the score refers only to the positive peak (see results).
[c]similar data for SFCM vectors Most of the DCN-transduced cell lines expressed medium or high level of LNGFR (50–200 a.u.). The FACS profiles of DCN-transduced cell lines correlated with results obtained from Southern analysis, in that cell lines harboring a rearranged provirus in addition to an intact one showed biphasic curves, with a negative and a positive peak proportional to the relative intensity of the bands corresponding to intact and rearranged proviruses, respectively.

Expression of vector-specific RNAs in transduced cells (K562) was determined by Northern blotting of poly(A)+ RNA isolated from G418-selected cell lines, hybridized to LNGFR and Neo probes. The patterns obtained were consistent with the expected transcription profiles of each retroviral vector. In the NSV-N- and NTK-N-transduced cells, an unspliced and a spliced RNA species hybridized to both the LNGFR and Neo probe. The SV40- and TK-derived subgenomic transcripts containing the LNGFR-specific mRNA were observed only after hybridization to the LNGFR probe. LNSN-or SFCM-transduced cells expressed only the unspliced RNA form, hybridizing to both NeoR and LNGFR probe. This is consistent with the reported inactivation of the splice donor site in the LXSN vector, from which LNSN and SFCM were derived[5]. A shorter transcript, corresponding to the SV40-derived NeoR mRNA hybridized only to the NeoR probe.

The DCN vector generated two LTR-derived genomic transcripts, an unspliced and a spliced form, respectively. A third RNA species was transcribed from the ADA promoter, and most likely used as the major mRNA template for LNGFR synthesis. The relative contribution of the ADA promoter in the 5' or in the 3' LTR to the LNGFR transcript cannot be assessed by this technique. A slow-migrating RNA form might represent a read-through transcript initiated from the ADA promoter in the 5' LTR and terminated at the poly(A) addition site in the 3' LTR. Two additional, unaccounted RNA species hybridizing only to the NeoR probe were also detected. These transcripts, present in all DCN-transduced cell lines, were the only RNA species detected in Raji cells, which did not express LNGFR and carried only rearranged proviruses, as demonstrated by Southern blot analysis. It is therefore likely that these transcripts are specific for the rearranged provirus, lacking the ADAp-LNGFR minigene.

The RNA expression pattern observed in the other cell lines was comparable with that obtained from K562, with the only exception of the EBV-infected RIM cell line, which consistently showed high levels of SV40-derived transcripts, from NSV-N, LNSN and SFCM.

Efficiency of vector-mediated gene transfer into human PBLs

Human PBLs were infected by retroviral vectors under PHA and IL-2 stimulation. In order to estimate infection frequencies, 48 hrs after infection human T-cells were cultured under limiting dilution conditions (1 to $10^3$ cells/well). Infected and uninfected control cells were cultured in the presence or absence of 0.4 mg/ml of G418. Cell growth was evaluated 14 days after plating, when no surviving cells could be detected in wells containing uninfected cells cultured in the presence of G418. The overall infection frequency ranged from less than 1% to 5.1%, depending upon viral titer of vector supernatants. However, significant variability was observed between different donors. Efficiency of gene transfer can be increased by multiple infection cycles or by co-cultivation. Co-cultivation of PBLs with irradiated virus-producing cell lines for 48 hrs consistently provides good gene transfer efficiency (10–15%). Double fluorescence analysis of LNGFR and T-cell markers ruled out the possibility of a contamination by vector-producing cells in the LNGFR positive population. In the experiment, the frequence of LNGFR expression was entirely due to expression of the transduced gene by infected PBLs since all cells positive in FACS analysis were co-expressing the human CD3. Independently of initial efficiency of gene transfer, transduced PBLs can be selected to homogeneity either by negative selection with G418 or by positive immunoselection with magnetic beads coupled to a monoclonal antibody directed against the LNGFR. In the representative experiment, a single round of immunoselection was sufficient for separating the population of transduced cells from uninfected PBLs. Once the magnetic beads were removed, a homogeneous population of transduced lymphocytes was obtained without significant loss of transduced cells.

In order to evaluate the efficiency of viral vectors in infecting human PBLs, a number of PBL bulk cultures were independently transduced by exposure to supernatants containing the different retroviral vectors and selected by G418 for vector presence and expression. Ten of the vector-transduced cultures (2 by NSV-N, 3 by NTK-N, 2 by LNSN/SFCM and 3 by DCN) were analyzed for the proviral integrations by Southern blotting. Hybridization to the NeoR probe of representative Xba I, which cuts in both 5' and 3' LTRs of all vectors (FIG. 1), allows detection of the size of integrated proviruses, and with Bgl II, which cuts only in genoric DNAs, allows estimation of the number of integration sites. In all the lymphocyte cultures transduced by NSV-N, NTK-N, and LNSN/SFCM, only bands corresponding to the intact integrated proviruses were detected, whereas an additional band corresponding to a rearranged provirus was observed in all DCN-transduced cultures.

Finally, analysis of the proviral integrations revealed that NSV-N-, NTK-N- and LNSN-/SFCNI-transduced T-cell cultures were largely polyclonal, whereas DCN-transduced cultures were essentially oligoclonal, as indicated by the presence of a predominant band and only a few minor ones. As previously suggested, this is probably due to lower viral titer and could be circumvented by different gene transfer protocols including co-cultivation of target cells with vector-producing cell lines.

Vector-mediated expression of the LNGFR on human T-lynipliocytes

Cell surface expression of LNGFR was detected by FACS analysis in a total of 23 retroviral vector-transduced T-lymphocyte cultures (5 NSV-N-, 8 NTK-N-, 5 LNSN- and 5 DCN-transduced cell lines). LNGFR expression was low in all NSV-N-transduced cells, and in six out of eight NFK-N-transduced cell cultures. The remaining two NTK-N-transduced T-cell lines showed intermediate levels of LNGFR expression. Heterogeneous expression levels were observed in LNSN-SFCM cell cultures, with two lines expressing low levels, two intermediate levels, and one high levels of LNGFR. In DCN-transduced cells, four out of five lines expressed low levels and one intermediate levels of LNGFR.

In order to characterize the infected cells, we tested 13 transduced cell lines for expression of cell surface lymphocyte differentiation antigens, using monoclonal antibodies anti-CD4, CD8, CD5, B4, Leu7, CD25R and CD34. All tested cell lines scored positively for CD5 and CD25R expression and negatively for Leu7, B4 and CD34 expression (data not shown). Eight out of 13 analyzed cultures were $LNGFR^+/CD8^+$, one was $LNGFR^+/CD4^+$ and four were positive for LNGFR and contained different percentages of cells co-expressing CD8 and CD4. Predominance of the $CD8^+$ phenotype in the PHA and IL-2 stimulated cultures was also observed in the uninfected control cell lines, and probably represent a constant bias of the T-cell culture procedure. In general, we did not observe preferential transduction of particular cellular subsets by any of the four retroviral vectors.

T-cell clones were obtained from vector-transduced T-cell cultures by plating cells in limiting dilution (1000, 100 and 10 cells/well), taking into account an average infection frequency of approximately 1%. 72% of all the examined clones were $LNGFR^+/CD4^+$ and 28% $LNGFR^+/CD8^+$. Predominance of the $CD4^+$ phenotype was also observed in control, uninfected T-cells cloned from the same donors, and is considered a standard finding under our cloning conditions. Furthermore, retroviral transduction and LNGFR expression was achieved in double-positive, $CD4^+/CD8^+$ clones. These results demonstrate that retroviral infection might occur not only in mature $CD4^+$ and $CD8^+$ cells, but also in immature $CD4^{+/CD}8^+$ double positive peripheral blood lymphocytes.

Analysis of T-cell repertoire in vector-transduced T-lymphocytes

As shown above, Southern blot analysis of viral integrations demonstrated the polyclonal nature of the vector-infected T-cell cultures. This was fiurther confirmed by molecular analysis of T-cell receptor (TCR) β chain rearrangements on Xba I digested DNA samples hybridized to a probe specific for the TCRβ chain constant region. A polyclonal pattern, with no predominant bands in addition to the germline pattern, was detected in T-cell cultures transduced duced with NSV, NTK-N and LNSN/SFCM. The presence of limited numbers of predominant rearrangement bands was observed in DCN-infected cultures, as for oligoclonal cell populations.

Further confirmation to these observations was obtained by systematic analysis of the TCR Vβ-chain usage in transduced lymphocytes. After a single cycle of PBLs infection by vector-containing supernatants, followed by selection of transduced cells by G418, the total RNA of the selected lymphocyte population was reverse transcribed and the obtained DNA was subjected to PCR by the use of Vβ-Cβ specific oligonucleotides, and to anchor PCR utilizing a Cβ specific oligonucleotides as described in the methods section. Analysis of the amplified products by Vβ-specific oligonucleotides showed an identical repertoire as compared to the original control population of untransduced/unselected lymphocytes. Similar to the results of the Southern blot analysis of TCR-β chain rearrangements, low viral titers in vector supernatants produced limited Vβ repertoire (data not shown). This limitation of low titer vectors could be circumvented by multiple infection cycles or by co-cultivation of PBLs with the producer cell line.

References

1) Miller A. D.: Human gene therapy comes of age. Nature 357:455, 1992

2) Karlsson S.: Treatment of genetics defects in hematopoietic cell function by gene transfer. Blood 78:2481, 1991

3) Anderson, W. F.: Human gene therapy. Science 256:808, 1992

4) Gilboa E., Eglitis M. A., Kantoff P. W., Anderson W. F.: Transfer and expression of cloned genes using retroviral vectors. BioTechniques 4:504, 1986

5) Miller A. D., Rosman G. J.: improved retroviral vectors for gene transfer and expression. BioTechniques 7:980,1989

6) Hantzopoulos P. A., Sullenger B. A., Ungers G., Gilboa E.: Improved gene expression upon transfer of the adenosine dearninase minigene outside the transcriptional unit of a retroviral vector. Proc. Natl. Acad. Sci. USA 86: 3519, 1989

7) Kasid A., Morecki S., Aebersold P., Cometta K., Culver K., Freeman S., Director E., Lotze M. T., Blaese R. M., Anderson W. F., Rosenberg S. A.: Human gene transfer: characterization of human tumor-infiltrating lymphocytes as vehicles for retroviral-mediated gene transfer in man. Proc. Natl. Acad. Sci. USA 87:473, 1990

8) Culver K., Cometta K., Morgan R., Morecki S., Aebersold P., Kasid A., Lotze M., Rosenberg S. A., Anderson W. F., Blaese R. M.: Lymphocytes as cellular vehicles for gene therapy in mouse and man. Proc. Natl. Acad. Sci. USA 88:3155, 1991

9) Rosenberg S. A., Aebersold P., Cometta K., Kasid A., Morgan R. A., Moen R., Karson E. M., Lotze M. T., Yang J. C., Topalian S. L., Merino M. J., Culver K., Miller A. D., Blaese R. M., Anderson W. F.: Gene transfer into humans immunotherapy of patients with advanced melanoma, using tumor-infiltrating lymphocytes modified by retroviral gene transduction. New Eng. J. of Mod. 323:570, 1990

10) Morecki S., Karson E., Cometta K., Kasid A., Aebersold P., Blaese R. M., Anderson W. F., Rosenberg S. A.: Retrovirus-mediated gene transfer into $CD4^+$ and $CD8^+$ human T cell subsets derived from tumor-infiltrating lymphocytes and peripheral blood mononuclear cells. Cancer Immunol. Immunother. 32:342, 1991

11) Ferrari G., Rossini S., Giavazzi R., Maggioni D., Nobili N., Soldati M., Ungers G., Mavilio F., Gilboa E., Bordignon C.: An in vivo model of somatic cell gene therapy for human sever combined immunodeficiency. Science 251:1363, 1991

13) Ferrari G., Rossini S., Nobili N., Maggioni D., Garofalo A., Giavazzi R, Mavilio F., Bordignon C.: Transfer of the ADA gene into human ADA-deficient T-lymphocytes reconstitutes specific immune function. Blood 80:120, 1992

14) Sullenger B. A., Gallardo H. F., Ungers G. E., Gilboa E.: Overexpression of TAR sequences renders cells resistant to human immunodeficiency virus replication. Cell 63:601, 1990

15) Lee T. C., Sullenger B. A., Gallardo H. F., Ungers G. E., Gilboa E.: Overexpression of RRE-derived sequences inhibits HIV-1 replication in CEM cells. New Biol. 4:66, 1992

16) Johnson D., Lanahan A., Buck C. R, Seghal A., Morgan C., Mercer E., Bothwell M., Chao, M.: Expression and structure of the human NGF receptor. Cell 47:545, 1986

17) Keller G., Paige C., Gilboa E., Wagner E. F.: Expression of a foreign gene in myeloid and lymphoid cells derived from multipotent haematopoietic precursors. Nature 318: 149, 1985

18) Wiginton D. A., Kaplan D. J., States J. C., Akeson A. L., Perme C. M., Bilyk I. J., Vaughn A. J., Lattier D. L., Hutton J. J.: Complete sequence and structure of the gene for human adenosine deaminase. Biochem. 25:8234, 1988

19) Mann R., Mulligan R. C., Baltimore D.: Construction of a retrovirus packaging mutant and its use to produce helper-free defective retrovirus. Cell 33:153, 1983

20) Sambrook J., Fritsch E. F., Maniatis T.: Molecular cloning: a laboratory manual 2nd ed. 1989

21) Miller A. D., Buttimore C.: Redesign of retrovirus packaging cell lines to avoid recombination leading to helper virus production. Mol. Cell. Biol. 6:2895, 1986

22) Southern P. J., Berg P.: Trannsformation of mammalian cells to antibiotic resistance with a bacterial gene under control of the SV40 early region promoter. J. Mol. Appi. Genet. 1:327, 1982

23) Yanagi Y., Yoshikai Y., Leggett K., Clark S. P., Aleksander I., Mak T. W.: A human T cell-specificcDNA clone encodes a protein having extensive homology to immunoglobulin chains. Nature308:145, 1984

24) Chirgwin J. M., Przybyla A. E., MacDonald R. J., Rutter W. J.: Isolation of biologically active ribonucleic acid from sources enriched in ribonuclease. Biochem. 18:5294, 1979

25) Thomas P. S.: Hybridization of denatured RNA and small DNA fragments transferred to nitrocellulose. Proc. Natl. Acad. Sci. USA 77:5201, 1980

26) Chomczynski P., Sacchi N.: Single-Step Method of RNA Isolation by Acid Guanidinium Thiocyanate-Phenol Chlorofonn Extraction. Analytical Biochemistry 162:156, 1987

27) Loh E. Y., Elliot J. F., Cwirla S., Lanier L. L., Davis M. M.: Polymerase single-sided specificity: analysis of T cell receptor $\partial$ chain. Science 243:217, 1989

28) Choi Y., Kotzin B., Herron L, Callahan J., Marrack P., Kappler J.: Interaction of Staphylococcus aureus toxin "superantigens" with human T cells. Proc. Natl. Acad. Sci. USA, Vol. 86:8941, 1989

29) Rosenberg W. M. C., PAH. Moss, Bell J. I.: Variation in human T cell receptor V$\beta$ and J$\beta$ repertoire: analysis using anchor polymerase chain reaction. Eur. J. Inmmunol. 22:541, 1992

30) Bordignon C.: A clinical protocol for transfer of the ADA gene into bone marrow cells and peripheral blood lymphocyies for the treatment of patients affected by ADA deficient SCID. Human Gene Therapy (in press).

31) Areman E. M. et al: Bone Marrow and Stem Cell Processing: A Manual of Current Techniques, F.A. Davies Co., Philadelphia (1992)

32) Reddy et al., Molecular Brain Research 8 (1990) 137–141

We claim:

1. A method of detecting in a sample, transduced human cells that have been introduced into a human patient, said sample suspected of containing transduced cells and non-transduced host cells, said method comprising:
   (a) introducing into said patient, a set of human cells which have been transduced with a nucleic acid which encodes and expresses modified cell surface receptor ("marker"), wherein said marker is modified with respect to a counterpart unmodified cell surface receptor that (i) is a human transmembrane protein, and (ii) binds with a ligand and transduces a signal, and wherein said modified cell surface receptor is altered relative to said counterpart unmodified cell surface receptor such that it binds with said ligand but cannot transduce said signal as a result of said ligand binding;
   (b) obtaining a sample from a patient treated according to step (a), wherein said sample is suspected of containing transduced cells and non-transduced cells, and wherein said non-transduced host cells present in said sample normally do not express said unmodified cell surface receptor; and
   (c) detecting within said sample, the presence or absence of said marker on the cell surface of said transduced cells, to thereby detect said transduced cells in said sample.

2. A method according to claim 1, wherein said modified cell surface receptor is a modified LNGFR (low affinity nerve growth factor receptor).

3. A method according to claim 2, wherein said modified LNGFR has a deletion of amino acids 245 to the C-terminus relative to unmodified LNGFR.

4. A method according to claim 2, wherein said modified LNGFR is characterized by at least partial deletion of the nucleic acid region encoding the intracellular domain.

5. A method according to claim 1, wherein said modified cell surface receptor is a modified CD24-receptor.

6. A method according to claim 1, wherein said modified cell surface receptor is a modified LDL receptor.

7. A method according to claim 1, wherein in step (a) said set of human cells that are transduced in step (a) are T-lymphocytes and said modified cell surface receptor is a modified LNGFR.

8. A method according to claim 7, wherein step (c), further comprises isolating said transduced T-lymphocytes which express said marker.

9. A method according to claim 7, wherein said detecting comprises contacting said sample with anti-LNGFR antibodies to form antibody-bound-modified LNGFR complexes and determining the presence of said complexes as indicative of the presence of said marker.

10. A method according to claim 9, wherein said antibodies are labeled with a detectable label.

11. A method according to claim 10, wherein said detectable label is a fluorescein and wherein said detecting further comprises isolating said transduced cells by performing fluorescent activated cell sorting.

12. A method according to claim 1, wherein said set of human cells that have been transduced in step (a) are hematopoietic cells and said modified cell surface receptor is a modified LNGFR.

13. A method according to claim 12, wherein said hematopoietic cells, prior to having been transduced, are (I) obtained by explanting from said patient and (ii) prepared by purging to obtain a set of autologous hematopoietic cells substantially free of clonogenic tumor cells.

14. A method according to claim 13, wherein purging comprises treating with irradiation.

15. A method according to claim 13, wherein purging comprises treating with cytotoxic agents.

16. A method according to claim 13, wherein after step c), said patient has a tumor relapse, said method further comprising:

(d) determining the nature of a patient's relapse by obtaining tumor cells in said sample and detecting the presence or absence of marker in said tumor cells, wherein the presence of marker is indicative that relapse was caused by residual tumor cells in the transduced hematopoietic cells.

17. A set of T-lymphocytes for introduction into an allogeneic bone marrow transplant patient, comprising human T-lymphocytes having been transduced with a nucleic acid which encodes and expresses a modified cell surface receptor ("marker"), wherein said marker is modified with respect to a counterpart unmodified cell surface receptor that (i) is a human transmembrane protein, and (ii) binds with a ligand and transduces a signal, and wherein said modified cell surface receptor is altered relative to said counterpart unmodified cell surface receptor such that it binds with said ligand but cannot transduce said signal as a result of said ligand binding, such that said marker permits differentiation between transduced T-lymphocytes and non-transduced cells which do not normally express said unmodified cell surface receptor.

18. A cell according to claim 17, wherein said modified LNGFR is characterized by at least partial deletion of the nucleic acid region encoding the intracellular domain.

19. A cell according to claim 18, wherein said LNGFR has a deletion of amino acids 245 to the C-terminus relative to unmodified LNGFR.

20. An isolated hematopoietic cell obtained according to claim 12.

21. A set of cells according to claim 17, wherein said modified cell surface receptor is a modified LNGFR.

22. A set of human hematopoietic cells for introduction into an allogeneic bone marrow transplant patient, comprising human hematopoietic cells having been transduced with a nucleic acid which encodes and expresses a modified cell surface receptor ("marker"), wherein said marker is modified with respect to a counterpart unmodified cell surface receptor that (i) is a human transmembrane protein, and (ii) binds with a ligand and transduces a signal, and wherein said modified cell surface receptor is altered relative to said counterpart unmodified cell surface receptor such that it binds with said ligand but cannot transduce said signal as a result of said ligand binding, such that said marker permits differentiation between transduced human hematopoietic cells and non-transduced cells which do not normally express said unmodified cell surface receptor.

23. A set of cells according to claim 22, wherein said modified cell surface receptor is a modified LNGFR.

24. A set of human hematopoietic cells for introduction into an autologous bone marrow transplant patient, comprising human hematopoietic cells having been transduced with a nucleic acid which encodes and expresses modified cell surface receptor ("marker"), wherein said marker is modified with respect to a counterpart unmodified cell surface receptor that (i) is a human transmembrane protein, and (ii) binds with a ligand and transduces a signal, and wherein said modified cell surface receptor is altered relative to said counterpart unmodified cell surface receptor such that it binds with said ligand but cannot transduce said signal as a result of said ligand binding, such that said marker permits differentiation between transduced autologous hematopoietic cells and non-transduced cells which do not normally express said unmodified cell surface receptor.

25. A set of cells according to claim 24, wherein said modified cell surface receptor is a modified LNGFR.

* * * * *